US007943775B2

(12) United States Patent
Li et al.

(10) Patent No.: US 7,943,775 B2
(45) Date of Patent: May 17, 2011

(54) SMALL MOLECULES FOR IMAGING PROTEIN-PROTEIN INTERACTIONS

(75) Inventors: King C. Li, Bethesda, MD (US); S. Narasimhan Danthi, Germantown, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 932 days.

(21) Appl. No.: 11/762,579

(22) Filed: Jun. 13, 2007

(65) Prior Publication Data

US 2008/0085238 A1    Apr. 10, 2008

Related U.S. Application Data

(60) Provisional application No. 60/815,740, filed on Jun. 21, 2006.

(51) Int. Cl.
C07D 211/06 (2006.01)
A61K 49/00 (2006.01)
C07C 233/05 (2006.01)

(52) U.S. Cl. ......... 546/226; 424/1.65; 424/9.1; 424/9.3; 424/9.6; 568/13; 564/163

(58) Field of Classification Search ............... 424/1.65, 424/9.1, 9.3, 9.6; 546/226; 558/13; 564/163
See application file for complete search history.

(56) References Cited

U.S. PATENT DOCUMENTS

| | | | |
|---|---|---|---|
| 5,403,833 | A | 4/1995 | Calne |
| 5,516,797 | A | 5/1996 | Armistead et al. |
| 5,614,547 | A | 3/1997 | Hamilton et al. |
| 5,622,970 | A | 4/1997 | Armistead et al. |
| 5,665,774 | A | 9/1997 | Armistead et al. |
| 6,372,712 | B1 | 4/2002 | Briesewitz et al. |
| 7,169,816 | B2 * | 1/2007 | Barrett et al. ............... 514/615 |
| 7,238,682 | B1 * | 7/2007 | Rosen et al. ................ 514/183 |
| 2003/0207833 | A1 * | 11/2003 | Berkley et al. ............... 514/44 |
| 2004/0014087 | A1 * | 1/2004 | Hodgson et al. ............. 435/6 |
| 2005/0002859 | A1 * | 1/2005 | Marnett et al. .............. 424/1.11 |
| 2007/0203332 | A1 * | 8/2007 | Graupner ...................... 536/22.1 |

FOREIGN PATENT DOCUMENTS

| | | |
|---|---|---|
| WO | 0135748 A1 | 5/2001 |
| WO | 0135978 A1 | 5/2001 |

OTHER PUBLICATIONS

Yang et al, J. Med. Chem, 2000, 43, 1135-1142.*
Bose, M., et al., "Nature-inspired' drug-protein complexes as inhibitors of A beta aggregation," Biochem. Soc. Trans., 33(4): 543-547 (2005).
Braak, H., et al., "Neuropathological stageing of Alzheimer-related changes," Acta Neuropathol, 82: 239-259 (1991).
Braun, P.D., et al., "A Bifunctional Molecule that Displays Context-Dependent Cellular Activity," J. Am. Chem. Soc., 125: 7575-7580 (2003) (abstract only).
Gestwicki, J.E., et al., "Harnessing Chaperones to Generate Small-Molecule Inhibitors of Amyloid beta Aggregation," Science, 306: 865-869 (2004) (abstract only).
Graner, M.W., et al., "Chaperone proteins and brain tumors: Potential targets and possible therapeutics," Neuro-Oncology, 7: 260-277 (2005).
Keenan, T., et al., "Synthesis and Activity of Bivalent FKBP12 Ligands for the Regulated Dimerization of Proteins," Bioorganic & Medicinal Chemistry, 6: 1309-1335 (1998) (abstract only).
Meriin, A.B., et al., "Role of molecular chaperones in neurodegenerative disorders," Int. J. Hyperthermia, 21(5): 403-419 (2005) (abstract only).
Nordberg, A., "PET imaging of amyloid in Alzheimers disease," The Lancet, Neurology, 3: 519-527 (2004) (abstract only).
Whitesell, L., et al., "HSP90 and the Chaperoning of Cancer," Nature Reviews/Cancer, 5: 761-772 (2005) (abstract only).

* cited by examiner

*Primary Examiner* — Shailendra Kumar
(74) *Attorney, Agent, or Firm* — Cantor Colburn LLP

(57) ABSTRACT

A tissue is imaged to detect the presence of amyloid deposits or other target proteins prior to their aggregation into plaques, with the assistance of the administration of a labeled bifunctional compound of which one functionality binds to the target protein and the second functionality binds to a chaperone protein that is present in the tissue of interest. The two functionalities have different binding affinities, the target-binding functionality having the greater binding affinity, with the result that the bifunctional compound preferentially remains in the tissue when bound to the chaperone and then the target protein while bifunctional compound that is not bound to the target protein will leave the tissue. The inclusion of the chaperone allows the imaging process to detect the non-aggregated proteins by way of the label and the difference in kinetics of the binding to the chaperone and the target protein permits one to distinguish between binding of the bifunctional molecule to the chaperone only and binding to the chaperone and then to the target protein. Certain intermediates toward the synthesis of these bifunctional compounds are novel by themselves, and labeled bifunctional molecules in general that utilize a lysine linker are also disclosed as a novel class of compounds.

16 Claims, No Drawings

SMALL MOLECULES FOR IMAGING PROTEIN-PROTEIN INTERACTIONS

CROSS-REFERENCE TO RELATED APPLICATION

This application claims the benefit of U.S. Provisional Patent Application No. 60/815,740, filed Jun. 21, 2006, the contents of which are incorporated herein by reference in their entirety.

BACKGROUND OF THE INVENTION

1. Field of the Invention

This invention resides in the field of diagnostic methods and pharmaceutical agents associated with Alzheimer's disease.

2. Description of the Prior Art

Alzheimer's disease (AD) is the most common form of dementia, afflicting tens of millions of people worldwide, and with the high vulnerability of the elderly to this disease, the number of cases is increasing each year as life expectancy increases throughout the world. The debilitating characteristics of AD include irreversible memory impairment, continuous cognitive decline, and behavioral disturbances, and the disease presents a continuing challenge for society and for health care systems. Advances have been made in understanding the etiology, genetics, and pathophysiological mechanism for AD, but no cure has as yet been found.

It is known that AD is associated with the presence of senile plaques of amyloid β (Aβ) peptide and neurofibrillary tangles composed of hyperphosphorylated protein tau. The plaques are formed by the aggregation of the Aβ peptide, and the peptide itself is produced by the sequential proteolytic processing of amyloid precursor protein (APP) by β and γ secretases. Plaque formation is preceded by the accumulation of Aβ due to genetic mutations. A high level of Aβ is thus regarded as an initial pathogenetic factor for the development of neurodegeneration in AD.

Current efforts to control or prevent the development or progression of AD are directed toward prevention of Aβ plaque formation, primarily through the use of drugs that inhibit the aggregation of Aβ. Recent reports of such drugs appear in Bose, M., et al., "'Nature-inspired' drug-protein complexes as inhibitors of Aβ aggregation," *Biochem. Soc. Trans.* 2005, 33 (pt. 4), 543-547; Gestwicki, J. E., et al. "Harnessing Chaperones to Generate Small-Molecule Inhibitors of Amyloid β Aggregation," *Science* 306, 865-869 (29 Oct. 2004); Braun, P. D., et al., "A Bifunctional Molecule That Displays Context-Dependent Cellular Activity," *J. Am. Chem. Soc.* 2003, 125, 7575-7580; Briesewitz, R., et al., "Synthetic Bifunctional Molecules Containing a Drug Moiety and Presenter Protein Ligand," U.S. Pat. No. 6,372,712 B1, issued Apr. 16, 2002; Briesewitz, R., et al., "Bifunctional Molecules Having Modulated Pharmacokinetic Properties and Therapies Based Thereon," International Patent Application Publication No. WO 01/35748 A1, publication date May 25, 2001; and Briesewitz, R., et al., "Targeted Bifunctional Molecules and Therapies Based Thereon," International Patent Application Publication No. WO 01/35978 A1, publication date May 25, 2001.

The use of these drugs is most effective when combined with the detection of amyloid deposits prior to plaque formation, together with detection of the tissues in which the deposits reside. The relation of the tissues in which the amyloid deposits reside to the stage of the disease is described by Braak, H., et al., "Neuropathological staging of A beta deposition in the human brain and its relevance for the development of AD," *J. Neural Trans. Suppl.* 1991, 82, 239-259, who report that amyloid deposits first appear in the basal neocortex, then spread to all areas of the cortex, and subsequently to subcortical brain regions including the cerebellum. If the deposits are detected in the basal cortex, therefore, the proper administration of drugs can prevent progression to the other areas of the cortex and of the brain in general.

The existence and location of amyloid deposits has been detected by conventional imaging techniques, notably positron emission tomography (PET) and single photon emission computerized tomography (SPECT), enhanced by the administration of imaging agents that demonstrate binding specificity for Aβ. Agents that have been developed for this purpose are radiolabeled antibodies to Aβ and radiolabeled peptide fragments, as well as small molecules such as derivatives of Congo red (sodium salt of benzidinediazo-bis-1-naphthylamine-4-sulfonic acid), thioflavin, stilbene, and acridine. The use of these imaging agents is reported by Nordberg, A., "PET imaging of amyloid in Alzheimer's disease," *The Lancet, Neurology* 3, 519-527 (September 2004). Prominent among these agents are 2-(1-{6-[(2-[$^{18}$F]fluoroethyl)(methyl)amino]-2-naphthyl}ethylidene)malononitrile ($^{18}$F-FDDNP) and 2-(4'-[$^{11}$C]methylaminophenyl)-6-hydroxy-benzothiazole ($^{11}$C-PIB).

The effectiveness of small molecule imaging agents is limited, since their small size allows them to easily penetrate the blood-brain barrier, causing these agents to have a wide biodistribution. As a result, these agents remain in the tissue of interest for only a short period of time, too short in many cases for effective detection of Aβ. They are therefore useful primarily for the detection of plaques, rather than pre-plaque Aβ proteins.

By binding to Aβ, these imaging agents act in a manner similar to the drugs referenced above. A notable distinction that is evident from the publications set forth above is that the inhibitory effect of the drugs has been enhanced by combining the drugs with chaperone proteins. Chaperone proteins, which are endogenous to many tissues, are widely known for providing beneficial cellular effects due to their ability to bind to various types of normal and abnormal proteins, including those associated with neurodegenerative diseases. Indeed, one natural function that certain endogenous chaperone proteins serve by their binding ability is to prevent protein aggregation. In the context of drug administration as described in the above-referenced publications, the chaperone protein serves a dual purpose—it increases the affinity of the drug for Aβ (in this capacity the chaperone protein is referred to as a "presenter protein") and it blocks a large portion of the contact surface of the Aβ, thereby adding to the steric inhibition that the drug itself creates. The drug and chaperone are joined by a bifunctional molecule of which one functionality binds to the drug and a second functionality binds to the chaperone. To allow the chaperone to complement the drug effectively, the bifunctional molecule must have a high binding affinity for both the drug and the chaperone.

One might therefore apply similar reasoning to the imaging problem and combine the imaging agent with a chaperone protein. The added bulk achieved by the binding of the chaperone might theoretically reduce the undesirable rapid transit of the imaging agent through the tissue of interest, and the added affinity to the target due to the attachment of the chaperone might increase the binding affinity of the agent and chaperone together to pre-plaque Aβ, thereby increasing the detectability of the Aβ proteins. Accordingly, one might contemplate taking bifunctional molecules proposed for the therapeutic inhibitory effect, derivatizing the molecules by adding a detectable, e.g., radioactive, label, and using them for imaging. Effective imaging is not well served, however, by a bifunctional molecule that is effective for inhibition of plaque formation. Since the bifunctional molecule for effective inhibition binds strongly to both the target (Aβ) and the chaperone, the label will appear on three different complexes—the complex formed by the target and the bifunctional molecule alone, the complex formed by the bifunctional molecule and the chaperone alone, and the complex formed by all three, i.e., the target, the bifunctional molecule, and the chaperone. One will then be unable to distinguish between these three complexes and thereby detect the presence of Aβ by simply detecting the label.

SUMMARY OF THE INVENTION

The present invention resides in bifunctional molecules for imaging proteins of low concentration in vivo. The molecules are constructs that contain a portion that binds to the target protein, a portion that binds to the chaperone, a linking group, and a label. Each construct has a differential binding affinity between the target-binding and chaperone-binding portions whereby the target-binding portion has a stronger binding affinity than the chaperone-binding portion. The target-binding portion can thus be characterized as having a slow-on/slow-off binding interaction, and the chaperone-binding portion can be characterized as having a fast-on/fast-off binding interaction. This combination of different binding affinities favors the binding of the construct to both the target protein and the chaperone but with different kinetics. By analyzing the time course of detection of the label one can distinguish between the binding of the bifunctional molecule to the chaperone alone vs. the binding of the bifunctional molecule first to the chaperone and then to the target protein. The latter is a reliable indicator of the presence of the target protein.

In the following description, amyloid deposits are used as the target protein and are a preferred subclass of target proteins. It will be readily apparent that a wide variety of other target proteins can be substituted, with appropriate choices of chaperone and the binding portions of the bifunctional molecule.

The present invention also resides in certain novel intermediates useful in the formation of bifunctional molecules for imaging amyloid deposits. One class of intermediates are derivatized forms of flufenamic acid. These derivatized forms have the general formula

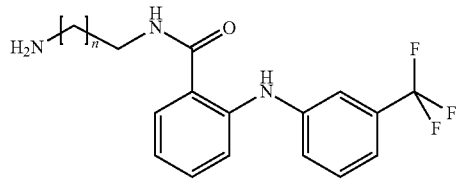

wherein n is 1, 2, 3, or 4. Preferred values of n are 2, 3, and 4, more preferred are 2 and 3, and the most preferred is 2. While flufenamic acid in its underivatized form is known to have binding affinity to amyloid β, the inventors herein have discovered that these derivatives have binding affinity to amyloid β as well. Because of the difference in structure entailed by the derivatization, this affinity is not predictable.

The present invention further resides in three novel optical isomers of (1R)-1-[4-(carboxymethoxy)phenyl]-3-(3,4-dimethoxy-phenyl)-1-propanyl (2S)-1-(3,3-dimethyl-1,2-dioxopentyl)-2-piperidinecarboxylate, a compound already known for its binding affinity to certain chaperone proteins. These novel optical isomers are

9-RR

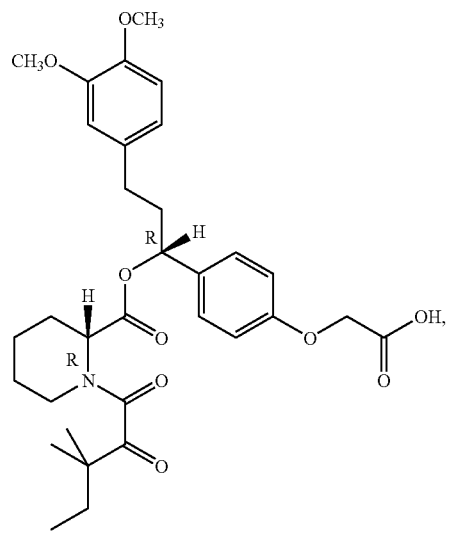

9-SR

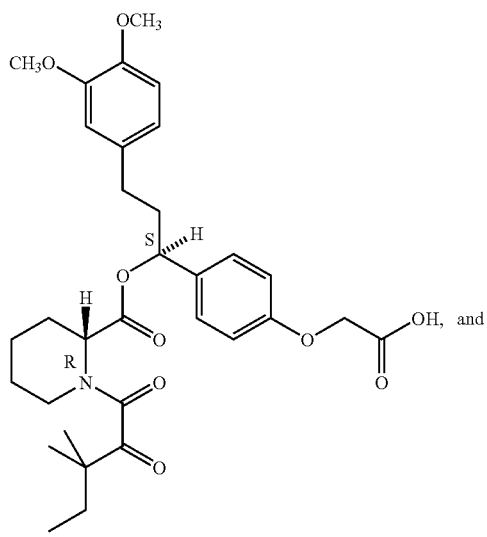

and

9-SS

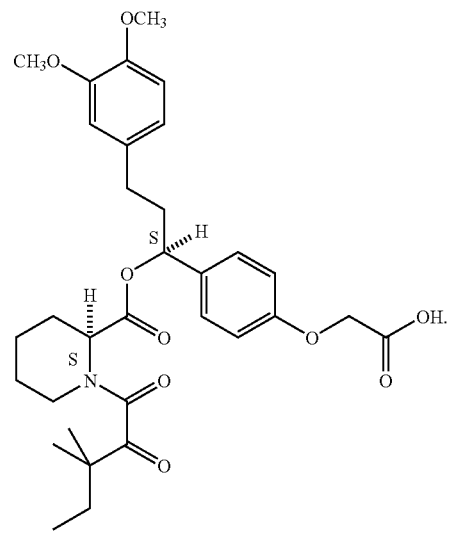

A discovery associated with these new isomers is that each binds differentially to different chaperones.

Further still, this invention also resides in a novel labeled bifunctional molecule for imaging a target protein in vivo, consisting of a moiety having binding specificity and affinity for a target protein, another moiety having binding specificity and affinity for a chaperone protein, a detectable label, and a lysine moiety serving as a linking group joining said both binding moieties and the detectable label. The target protein and chaperone protein binding moieties in this aspect of the invention are not limited to any particular range of binding affinities. Thus, bifunctional molecules in which the target-binding moiety has a stronger binding affinity for the target than the chaperone-binding moiety has for the chaperone are included within this aspect of the invention, as are bifunctional molecules in which the relative binding affinity strengths are reversed and those in which both moieties have the same or approximately the same binding affinities. A preferred structure for the labeled bifunctional molecule is

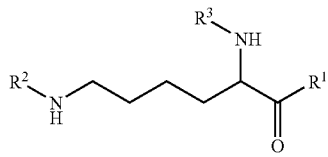

wherein $R^1$ is the target-binding moiety, $R^2$ is the chaperone-binding moiety, and $R^3$ is the detectable label. Preferred detectable labels are fluorophores, and preferred target-binding moieties are those that bind amyloid β.

DETAILED DESCRIPTION OF THE INVENTION AND PREFERRED EMBODIMENTS

Actual values of the binding affinities of the target-binding portion and the chaperone-binding portion of the construct of the present invention can vary widely and are not critical. The characteristic feature of this invention is the relative binding affinities of the two moieties, the target-binding portion having a substantially higher binding affinity than the chaperone-binding portion. The binding affinities can be expressed in the conventional manner, in units of molarity, as used in the prior art for binding affinities to proteins, such as for antibody-antigen binding or ligand-receptor binding, and the relative affinities as molarity ratios. Thus, in preferred embodiments, the ratio of binding affinities of the target-binding portion to the chaperone-binding portion will range from about $10^{-1}$ to about $10^{-6}$, and most preferably from about $10^{-2}$ to about $10^{-4}$. In absolute terms, the binding affinity of the target-binding portion preferably resides in the range of about $10^{-5}$ M to about $10^{-10}$ M, and most preferably in the ranges of about $10^{-6}$ M to about $10^{-10}$ M, about $10^{-5}$ M to about $10^{-9}$ M, or about $10^{-6}$ M to about $10^{-9}$ M, while the binding affinity of the chaperone-binding portion preferably resides in the range of about $10^{-2}$ M to about $10^{-8}$ M, and most preferably in the range of about $10^{-3}$ M to about $10^{-7}$ M.

The chaperone-binding portion can be any ligand that binds to the chaperone in the tissue of interest at the desired level of binding affinity. Appropriate chaperones for targets that are β-amyloid molecules will be those that bind to β-amyloid molecules, and such chaperones are known in the art. Prominent examples of these chaperones are members of the peptidyl-prolyl cis-trans isomerase family, particularly the FKBP and cyclophilin proteins. Chaperones that are members of the FKBP group are preferred. Examples of ligands that will serve as the binding portion of the construct for these chaperones, i.e., that will serve as $R^1$, are FK506, rapamycin, cyclosporin A, and synthetic ligands of FKBP and cyclophilin proteins, such as FK1012 and others. Disclosures of synthetic ligands are found in Armistead, D. M., et al., U.S. Pat. No. 5,665,774, issued Sep. 9, 1997; Armistead, D. M., et al., U.S. Pat. No. 5,622,970, issued Apr. 22, 1997; Armistead, D. M., et al., U.S. Pat. No. 5,516,797, issued May 4, 1996; Hamilton, G. S., et al., U.S. Pat. No. 5,614,547, issued Mar. 25, 1997; and Calne, R., U.S. Pat. No. 5,403,833, issued Apr. 4, 1995. Further ligands are (1R)-1-[4-(carboxymethoxy)phenyl]-3-(3,4-dimethoxy-phenyl)-1-propanyl (2S)-1-(3,3-dimethyl-1,2-dioxopentyl)-2-piperidinecarboxylates, particularly the optical isomers noted above.

The amyloid-binding portion can be any moiety that has the appropriate binding specificity and affinity. As noted above, a variety of amyloid imaging ligands are known, as listed in the references cited above, notably the Nordberg et al. paper, and either these or analogs that are not radiolabeled and not fluorescent and have binding affinities in the desired range can be used. Examples of the known ligands are Congo red, chrysamine-G, thioflavin-S, thioflavin-T, X-34 (a fluorescent derivative of Congo red), TZDM (2-(4'-dimethylaminophenyl)-6-iodobenzothiazole), IMSB ((E,E)-1-iodo-2,5-bis(3-hydroxycarbonyl-4-hydroxy)styrylbenzene), FDDNP (2-(1-{6-[(2-fluoroethyl)(methyl)amino]-2-naphthyl}ethylidene)malononitrile), C-4, BTA-1(2-(4"-(methylamino)phenyl)benzothiazole), and N-methyl-PIB.

The various moieties for the target-binding and chaperone-binding portions are residues of the species listed above. The term "residue" is used herein to denote that the portions are the sections of the molecules in each case that remain after covalent linkages have been made between these molecules and the linker group. The portion of the molecule in each case that remains as the residue will be readily apparent to anyone skilled in organic chemistry couplings and conjugations involving these types of molecules.

The amyloid-binding portion and the chaperone-binding portion of the constructs of the present invention are joined together by a linking group covalently bonded to each of the two portions. The linking group is preferably a group that is biologically inert and does not interfere with the binding specificities or affinities of either the amyloid-binding portion or the chaperone-binding portion. The linking group generally consists of a spacer moiety terminating at either end with a reactive functionality that is capable of forming a covalent bond with the amyloid-binding portion or the chaperone-binding portion, or both. Additional functionalities can also be present, particularly where the linking group serves as a site of attachment of a label. Examples of spacer moieties are aliphatic and unsaturated hydrocarbon chains, optionally including heteroatoms such as oxygen and nitrogen, either interrupting the carbon chains or at the termini of the chains. Further examples are peptides and carbohydrates. Still further examples will be apparent to those skilled in the art. A lysine residue is a particularly preference linking group.

The choice of linking group can itself affect the binding affinities of the amyloid- and chaperone-binding portions of the construct. The length of the linking group, for example, can affect steric, and possibly electrostatic, interactions between the chaperone and the amyloid deposit as well as the proximity that can be achieved between the chaperone and the amyloid deposit.

The label can be attached to either the amyloid-binding portion, the chaperone-binding portion, or the linking group. Attachment can be achieved by covalent binding, electrostatic binding, or any intermolecular attraction force that will maintain a joinder between the label and the remainder of the construct. If the label is attached to either the amyloid-binding portion or the chaperone-binding portion, the label is preferably attached in such a manner that the binding affinity of the portion to which the label is attached is not significantly impaired by the label. Preferably, the label is covalently bonded to the linking group.

The type of label used can vary widely, and its selection will be based on the type of imaging method to be used. Fluorescent labels can thus be used, as can radioactive isotopes and contrast agents for magnetic resonance spectroscopy or imaging. Examples of useful imaging methodologies include fluorescence imaging, single photon emission computed tomography (SPECT), position emission tomography (PET), magnetic resonance imaging (MRI), and computerized tomography (CT) scans. Any label known in the art, including those listed in the documents referenced above, can be used.

The imaging agents of the present invention can be administered in conventional types of formulations that are known in the art for imaging agents. The formulations will typically include carriers, diluents, binders, dispersing agents, lubricants, buffering agents, and preservatives, and can assume the form of tablets, capsules, solutions, suspensions, and the like, for oral, parenteral, intravenous, or other conventional types of administration. The dosages will be any amount that is effective in producing a detectable image with little or no undesirable side effects, and that will remain in the tissue of interest for a sufficient period of time to allow reliable imaging, and then be excreted from the body.

Tissue specificity in the imaging procedure is achieved in any of a variety of ways. One way is by the use of localized imaging, using a technique that allows the identification of the tissue from the image itself or the manner in which the image is obtained. A second way is by selecting a construct of a particular physicochemical property such as lipid solubility and partition coefficient $pK_a$, molecular weight and molecular volume, aqueous solubility, and chemical stability, where such physicochemical properties will affect the biodistribution of the construct. Such properties can be chosen in a manner that will cause the construct to favor the tissue of interest over other tissues. A third way is by selection of a chaperone-binding portion that will bind to chaperones that are upregulated in diseased or specific tissues. Disclosures of chaperones that are associated with certain diseases, tissues, or both, are found in Whitesell, L., et al., "HSP90 and the Chaperoning of Cancer," *Nature Reviews/Cancer* 5: 761-772 (October 2005); Graner, M. W., et al., "Chaperone proteins and brain tumors: Potential targets and possible therapeutics," *Neuro-Oncology* 7: 260-277 (2005); Meriin, A. B., et al., "Role of molecular chaperones in neurodegenerative disorders," *Int. J. Hyperthermia* 21(5): 403-419 (August 2005). As with all other documents cited in this specification, these papers are incorporated herein by reference.

Example 1

Synthesis of Candidates for the β-Amyloid Binding Portion

A two-part reaction scheme was used to prepare flufenamic acid derivatives with aminoalkyl groups of various lengths (established by different values of n in the formulas shown below), as examples of the β-amyloid binding portion of a bi-functional molecule of the present invention. The first part of the reaction scheme was as follows:

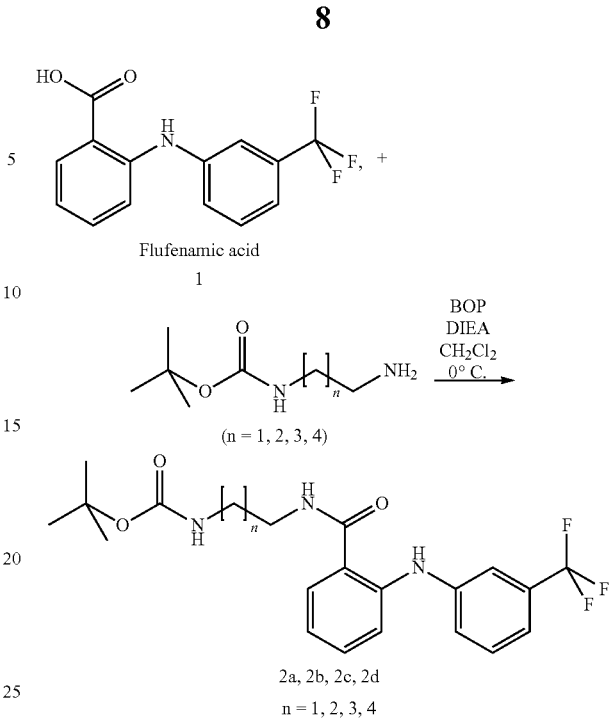

This reaction was performed by adding diisopropylethylamine (1.045 mL) in dropwise manner to a stirred solution of flufenamic acid (1, 562.5 mg, 2.0 mmol) and BOP reagent (benzotriazol-1-yl-oxy-tris-(dimethylamino)phosphonium hexafluorophosphate, 1.769 g, 4 mmol) in dry dichloromethane (10 mL) at 0° C. under argon. After stirring the reaction mixture for 30 min while still at 0° C., the N-boc-protected diamine (5 equivalents), where n=1, 2, 3, or 4, was added. The mixture was then warmed to room temperature and stirred for 30 h. The solvent was removed in vacuo and the remaining residue was dissolved in ethyl acetate and washed with saturated aqueous $NaHCO_3$ or 1M NaOH solution (3×10 mL) and water (10 mL), then dried over $MgSO_4$. The solvent was then removed in vacuo to yield a product that was then purified by flash chromatography ($CH_2Cl_2$:MeOH, 5%). The identities of the products for the different values of n were verified by analytical results as follows:

For n=1, the product (2a) was {2-[2-(3-trifluoromethyl-phenylamino)-benzylamino]-ethyl}-tert-butyl carbamate, a white powder, 770.5 mg (85%). $^1H$ NMR ($CDCl_3$, 300 MHz): δ 1.43 (s, 3H, Me), 3.41 (brs, 2H, $CH_2$), 3.52 (brs, 2H, $CH_2$), 6.83 (t, 1H, J=6.8 Hz), 7.20-7.44 (m, 6H), 7.38-7.44 (d, J=7.6 Hz). $^{13}C$ NMR ($CDCl_3$, 75 MHz): δ 28.29, 39.97, 41.61, 80.07, 115.78, 116.08 (q, J=3.7 Hz), 118.21 (q, 3.7 Hz), 118.92, 119.14, 122.74, 124.08 (q, J=272 Hz), 128.07, 129.78, 131.64 (q, J=32 Hz), 132.26, 142.47, 144.27, 157.46, 169.87; MS ($FAB^+$) m/z (%)=847.4 (($2M+H)^+$, 36%), 423.2 (M+, 52%), 264 (100%); HRMS ($FAB^+$) calcd for: $C_{21}H_{24}N_3O_3F_3$ 423.17698, recorded: 423.1770. Anal. calcd for: C, 59.57; H, 5.71; N, 9.92; F, 11.34. found C, 59.15; H, 6.19; N, 9.24; F, 14.00.

For n=2, the product (2b) was {2-[2-(3-trifluoromethyl-phenylamino)-benzylamino]-propyl}-tert-butyl carbamate, a faint yellow oil, 643 mg (74%). $^1H$ NMR ($CDCl_3$, 300 MHz): δ 1.37 (s, 3H, Me), 1.64 (s, 2H, $CH_2$), 3.14 (d, J=4.6 Hz, 2H, $CH_2$), 3.40 (d, J=5.4 Hz, 2H, $CH_2$), 5.34 (t, 1H, J=6.1 Hz, NH), 6.76 (t, 1H, J=7.0 Hz), 7.09-7.30 (m, 6H), 7.55 (d, J=7.4 Hz, 1H), 7.64 (s, 1H, NH). $^{13}C$ NMR ($CDCl_3$, 75 MHz): δ 28.26, 29.75, 35.95, 36.99, 79.08, 115.58, 117.65 (q, J=3.7

Hz), 118.92, 119.07, 119.36, 122.20, 123.86 (q, J=272 Hz), 127.85, 129.53, 131.28 (q, J=32 Hz), 131.80, 142.34, 143.74, 156.73, 169.34; MS (FAB$^+$) m/z (%)=875.4 ((2M+H)$^+$, 32%), 437.3 (M+, 60%), 264 (100%); HRMS (FAB$^+$) calcd for: $C_{22}H_{26}O_3N_3F_3$ 437.1926, recorded: 437.1925. Anal. Calcd for: C, 60.40; H, 5.99; N, 9.61; F, 13.00. found: C, 59.96; H, 5.79; N, 9.67; F, 13.17.

For n=3, the product (2c) was {2-[2-(3-trifluoromethyl-phenylamino)-benzylamino]-butyl}-tert-butyl carbamate, a faint yellow oil, 643 mg (74%). $^1$H NMR (CDCl$_3$, 300 MHz): δ 1.37 (s, 3H, Me), 1.54 (m, 4H, CH$_2$) 3.08 (brs, 2H, CH$_2$), 3.37 (dd, J=6.2 Hz, 2H, CH$_2$), 6.76 (dt, J=1.2 Hz & 8.0 Hz, 1H), 7.12-7.36 (m, 5H), 7.47 (d, J=7.6 Hz, 1H). $^{13}$C NMR (CDCl$_3$, 75 MHz): δ 26.37, 27.57, 28.22, 39.33, 39.85, 79.12, 115.73, 117.99 (q, J=3.7 Hz), 119.04, 119.50, 122.44, 123.94 (q, J=272 Hz), 129.66, 131.47 (q, J=32 Hz), 131.98, 142.38, 143.89, 156.13, 169.35; MS (FAB$^+$) m/z (%)=903 (2M+H)$^+$, 2.1%), 451 (M+, 46%), 264 (100%); HRMS (FAB$^+$) calcd for $C_{23}H_{28}O_3N_3F_3$ 451.2083, found 451.2080; calcd C, 61.19; H, 6.25; N, 9.31. found C, 61.12; H, 6.05; N, 9.61.

For n=4, the product (2d) was {2-[2-(3-trifluoromethyl-phenylamino)-benzylamino]-pentyl}-tert-butyl carbamate, a faint yellow oil, 768.6 mg (83%). $^1$H NMR (CDCl$_3$, 300 MHz): δ 1.38-1.60 (m, 15H, 3CH$_2$ & 3Me), 3.07-3.09 (m, 2H, CH$_2$) 3.30 (q, 2H, J=6.5 Hz, CH$_2$), 6.33 (s, 1H), 6.71 (t, 1H, J=6.5 Hz), 7.07-7.45 (m, 6H). $^{13}$C NMR (CDCl$_3$, 75 MHz): δ 24.00, 28.32, 29.63, 29.78, 39.69, 40.15, 79.08, 115.87, 118.11 (q, J=3.7 Hz), 119.15, 119.68, 122.21, 122.57, 124.02 (q, J=272 Hz), 127.68, 129.73, 131.58 (q, J=32 Hz), 132.07, 142.44, 143.99, 156.11, 169.39; MS (FAB$^+$) m/z (%)=931 (2M+H$^+$, 0.4), 465 (M$^+$, 30), 409 (21), 366 (39), 264 (100); HRMS (FAB$^+$) calcd for $C_{24}H_{30}O_3N_3F_3$ 465.2239, found 465.2237; calcd C, 61.92; H, 6.50; N, 9.03; F, 12.24. found C, 59.74; H, 6.14; N, 8.74; F, 12.43.

The second part of the reaction scheme was as follows:

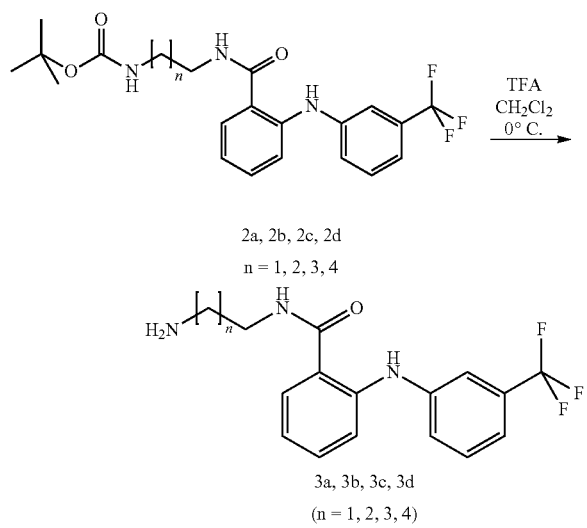

2a, 2b, 2c, 2d
n = 1, 2, 3, 4

3a, 3b, 3c, 3d
(n = 1, 2, 3, 4)

This reaction was performed by stirring a mixture of the product from the first part and trifluoroacetic acid in dichloromethane at 0° C. for 7 h. The trifluoroacetic acid was then removed in vacuo. Product verification was as follows:

For n=1, the product (3a) was N-(2-amino-ethyl)-2-(3-trifluoromethyl-phenylamino)-benzamide, a white powder. $^1$H NMR (D$_2$O, 300 MHz): δ 2.99 (t, 2H, J=6.1 Hz, CH$_2$) 3.47 (t, 2H, J=6.1 Hz, CH$_2$), 7.04 (t, 1H, J=7.44 Hz), 7.04-7.36 (m, 6H), 7.557 (d, J=7.8 Hz, 1H). $^{13}$C NMR (CDCl$_3$, 75 MHz): δ 36.96, 38.94, 114.56 (q, J=3.7 Hz), 117.73, 120.63, 120.78, 121.84, 123.94 (q, J=272 Hz), 128.93, 129.79, 130.85 (q, J=32 Hz), 132.49, 142.17, 142.80, 171.31. LRMS (ES$^+$): (M+H)$^+$ 324, (ES$^-$): (M–H)$^-$ 322.

For n=2, the product (3b) was N-(2-amino-propyl)-2-(3-trifluoromethyl-phenylamino)-benzamide, a white powder. $^1$H NMR (MeOD, 300 MHz): δ 1.78 (m, 2H, CH$_2$), 2.82 (t, 2H, J=7.2 Hz, CH$_2$) 3.31 (t, 2H, J=6.5 Hz, CH$_2$), 7.04 (t, 1H, J=7.44 Hz), 7.12-7.58 (m, 7H). $^{13}$C NMR (MeOD, 75 MHz): δ 27.37, 35.86, 36.97, 114.68 (q, 3.7 Hz), 116.80, 117.38 (q, J=3.7 Hz), 119.90, 120.76, 121.66, 122.02, 124.16 (q, J=272 Hz), 128.21, 128.54, 131.36 (q, J=32 Hz), 131.98, 143.12, 143.25, 170.78. LRMS (ES$^+$): (M+H)$^+$ 338, (ES$^-$): (M–H)$^-$ 336.

For n=3, the product (3c) was N-(2-amino-butyl)-2-(3-trifluoromethyl-phenylamino)-benzamide, a white powder. $^1$H NMR (D$_2$O, 300 MHz): δ 1.42-1.58 (m, 4H, CH$_2$), 2.87 (brs, 2H, CH$_2$), 3.13 (brs, 2H, CH$_2$), 6.56-6.92 (m, 7H), 7.36 (d, J=5.6 Hz, 1H). $^{13}$C NMR (D$_2$O, 75 MHz): δ 24.38, 25.68, 38.87, 39.09, 114.59, 116.10, 117.58, 119.84, 120.16, 121.57, 123.90 (q, J=272 Hz), 128.50, 130.35 (q, J=32 Hz), 131.89, 142.11, 142.42, 170.09. LRMS (ES$^+$): (M+H)$^+$ 352, (ES$^-$): (M–H)$^-$ 350.

For n=4, the product (3d) was N-(2-amino-pentyl)-2-(3-trifluoromethyl-phenylamino)-benzamide, a white powder. $^1$H NMR (D$_2$O, 300 MHz): δ 1.20-1.52 (m, 6H, 3CH$_2$), 3.00 (t, J=6.7 Hz), 2H), 3.30 (q, 6.5 Hz, 2H, CH$_2$), 6.3 (brs, 1H, NH), 6.71 (t, J=6.5 Hz, 1H), 7.09-7.45 (m, 7H). $^{13}$C NMR (D$_2$O, 75 MHz): δ 23.25, 26.49, 28.13, 39.30, 114.34, 116.64, 117.46, 120.18, 120.89, 123.93 (q, J=272 Hz), 128.54, 129.62, 130.22, 133.95 (q, J=32 Hz), 142.20, 142.45, 169.94. LRMS (ES$^+$): (M+H)$^+$ 366, (ES$^-$): (M–H)$^-$ 364.

Example 2

Screening of Candidates for the β-Amyloid Binding Portion

The four compounds 3a, 3b, 3c, and 3d prepared in Example 1 were tested for their suitability as candidates for the β-amyloid binding portion of the construct of this invention by two assays—an ELISA (enzyme-linked immunosorbent assay) and a dose-response assay. The assays and the results obtained are described below.

A. ELISA Assay

Step 1. Sample Solution Preparations. For each test compound, four samples and two standard solutions using Thioflavin-T as the standard were prepared in a coating buffer, each to a final concentration of 1 μM. The coating buffer was 50 mM Tris (Trizma Base from Sigma Aldrich, Inc., St. Louis, Mo., USA), 150 mM NaCl, 1 mM CaCl$_2$, 1 mM MgCl$_2$, and 1 mM MnCl$_2$, pH=7.4.

Step 2. Coating the Plate. The sample solutions were applied to individual wells of a 96-well polystyrene microtiter plate at 100 μL/well. The plates were sealed and allowed to incubate at 4° C. for at least 8 hours.

Step 3. Washing the Plate. The sample solutions were removed and the plate was washed two times with 300 μL/well of washing solution, which consisted of a 1 to 25 dilution in water of DELFIA® Wash Concentrate (PerkinElmer Life Sciences, Inc., Boston, Mass., USA).

Step 4. Blocking. Blocking was achieved by adding 150 μL/well of a blocking buffer which consisted of a 1 to 20 dilution in water of Milk Diluent/Blocking Solution Concentrate (from KPL, Inc., Gaithersburg, Md., USA). The plate was then incubated at room temperature for 2 hours.

Step 5. Sampling. Biotin-labeled amyloid-β was dissolved in a binding buffer to form a 1 μM solution of the amyloid-β. The binding buffer was a mixture of a coating buffer with the blocking buffer of Step 4 in a 90:10 ratio by volume. The coating buffer consisted of 50 mM Tris (Trizma Base from Sigma-Aldrich), 150 mM NaCl, 1 mM $CaCl_2$, 1 mM $MgCl_2$, 1 mM $MnCl_2$, pH=7.4 in redistilled water. Once blocking had been completed in Step 4, the blocking buffer was removed from each well, and the biotin-labeled amyloid β solution was placed in one of the wells for each of the four test compounds, together with additional blocking buffer for a total volume of 125 μL in the well. Dilutions were then prepared to achieve final concentrations per well of 40 μM, 30 μM, 20 μM, 10 μM, 5 μM, and 1 μM. The dilutions were performed in quadruplicate, thus resulting in four sets of wells for each test compound.

Step 6. Mixing. The solution in each well was mixed by being drawn into and ejected from a pipette 15 times. The plate was then gently agitated for further mixing. The plate was then covered and incubated at room temperature overnight.

Step 7. Washing. The solution in each well was discarded and the plate was washed three times with 170 μL/well of the washing solution described above.

Step 8. Binding with avidin-HRP. NeutrAvidinHRP solution was added to each well at 0.01 μg/well. The wells were then covered and incubated at room temperature for 30 minutes.

Step 9. Substrate addition. The solution in each well was discarded and the plate was washed 3 times with the above-referenced washing solution at 170 μL/well of washing solution. A chemiluminescent substrate solution which was a mixture of equal volumes of LumiGLO Substrate A and LumiGLO Substrate B from KPL, Inc., was then added at 100 μL/well.

Step 10. Fluorescence measurement and calculations. Luminescence was read on a Wallac Victor 1420 Multilabel Reader (PerkinElmer Life Sciences, Inc., Boston, Mass., USA). A plot of average luminescence vs. concentration was generated using KaleidaGraph (version 3.5) software and the $IC_{50}$ values were calculated using the following $$\text{Max}-\text{Max}*M0\hat{\ }m1(m2\hat{\ }m1+M0\hat{\ }m1); m1=1; m2=1,$$

where Max is the maximum luminescence observed. Average luminescence concentrations in counts per second (CPS) for each of the four β-amyloid-binding portion candidates at each dilution of the biotin-labeled β-amyloid are shown in Table I below.

TABLE I

ELISA Test Results for Candidates for β-Amyloid Binding Portion

| β-Amyloid Dilution (μL/well) | Test Compound: | Average Luminescence Concentration (CPS) | | | | |
|---|---|---|---|---|---|---|
| | | 3a | 3b | 3c | 3d | Thioflavin-T |
| 1 | | 323 | 878 | 32 | 105 | 940 |
| 5 | | 816 | 1325 | 74 | 220 | 570 |
| 10 | | 1453 | 1694 | 3128 | 678 | 731 |
| 20 | | 2072 | 2184 | 161 | 1461 | 86 |
| 30 | | 3072 | 4629 | 2968 | 2662 | 2311 |
| 40 | | 2986 | 4788 | 3025 | 2579 | 5140 |

From these averages, an $EC_{50}$ value for each test candidate was determined. Since a low $EC_{50}$ indicates high binding affinity, the candidate with the lowest $EC_{50}$ is the most likely to possess the desired characteristics as the amyloid-binding portion of the construct of the present invention. The data indicate that of the four candidates tested, compound 3b had the lowest $C_{50}$ and hence the strongest binding affinity, and is therefore the most appropriate.

B. Dose Response Assay

Step 1. Coating the plate. The four compounds 3a, 3b, 3c, and 3d were diluted to 6 different concentrations in the same coating buffer used in the ELISA. The resulting solutions were applied to individual wells of a 96-well polystyrene microtiter plate at 100 μL/well. The plate was then sealed and allowed to incubate at 4° C. for at least 8 hours.

Step 2. Washing the plate. The sample solutions were then removed and the plate was washed twice with 300 μL/well of the same washing solution used in the ELISA.

Step 3. Blocking. The blocking buffer used in the ELISA was added at a volume of 150 μL/well, and the plate was incubated at room temperature for 2 hours.

Step 4. Sampling. The blocking buffer was removed and biotin-labeled amyloid P was added to each well at a concentration of 1 μM in the same binding buffer used in the ELISA. The solution in each well was then mixed by being drawn into and ejected from a pipette 15 times. The plate was then gently agitated for further mixing. After mixing, the plate was covered and incubated at room temperature overnight.

Step 5. Washing. The solution in each well was discarded and the plate was washed three times with 170 μL/well of the washing solution described above.

Step 6. Binding with avidin-HRP and substrate. NeutrAvidinHRP solution was added to each well at 0.01 μg/well. The wells were then covered and incubated at room temperature for 30 minutes. The solution in each well was discarded and the plate was washed 3 times with the above-referenced washing solution at 170 μL/well of washing solution. The chemiluminescent substrate solution of the ELISA was then added at 100 μL/well, and luminescence was read using the Wallac Victor 1420 Multilabel Counter.

Step 7. Reading and calculations. Values for average luminescence vs. concentration were developed in the same manner as in the ELISA. From these values were determined $EC_{50}$ values for each of the four test compounds as β-amyloid-binding portion candidates. The $EC_{50}$ values are shown in Table II below.

TABLE II

Dose-Response Test Results for Candidates for β-Amyloid Binding Portion

| | 3a | 3b | 3c | 3d |
|---|---|---|---|---|
| $EC_{50}$ | $5.042 \times 10^{-5}$ | $3.189 \times 10^{-5}$ | $3.6172 \times 10^{-5}$ | $3.584 \times 10^{-5}$ |

As in the ELISA, a low $EC_{50}$ indicates high binding affinity, and the candidate with the lowest $EC_{50}$ is the most likely to possess the desired characteristics as the amyloid-binding portion of the construct of the present invention. The data indicate that, as in the ELISA test results, compound 3b of the four candidates tested has the lowest $EC_{50}$ and hence the strongest binding affinity, and is therefore the most appropriate.

Example 3

Synthesis of Candidates for the Chaperone Binding Portion

The compound (1R)-1-[4-(carboxymethoxy)phenyl]-3-(3,4-dimethoxy-phenyl)-1-propanyl (2S)-1-(3,3-dimethyl-1,2-dioxopentyl)-2-piperidinecarboxylate (9) was synthesized for use as an example of the chaperone binding portion. The following reaction scheme was used for the preparation of this compound:

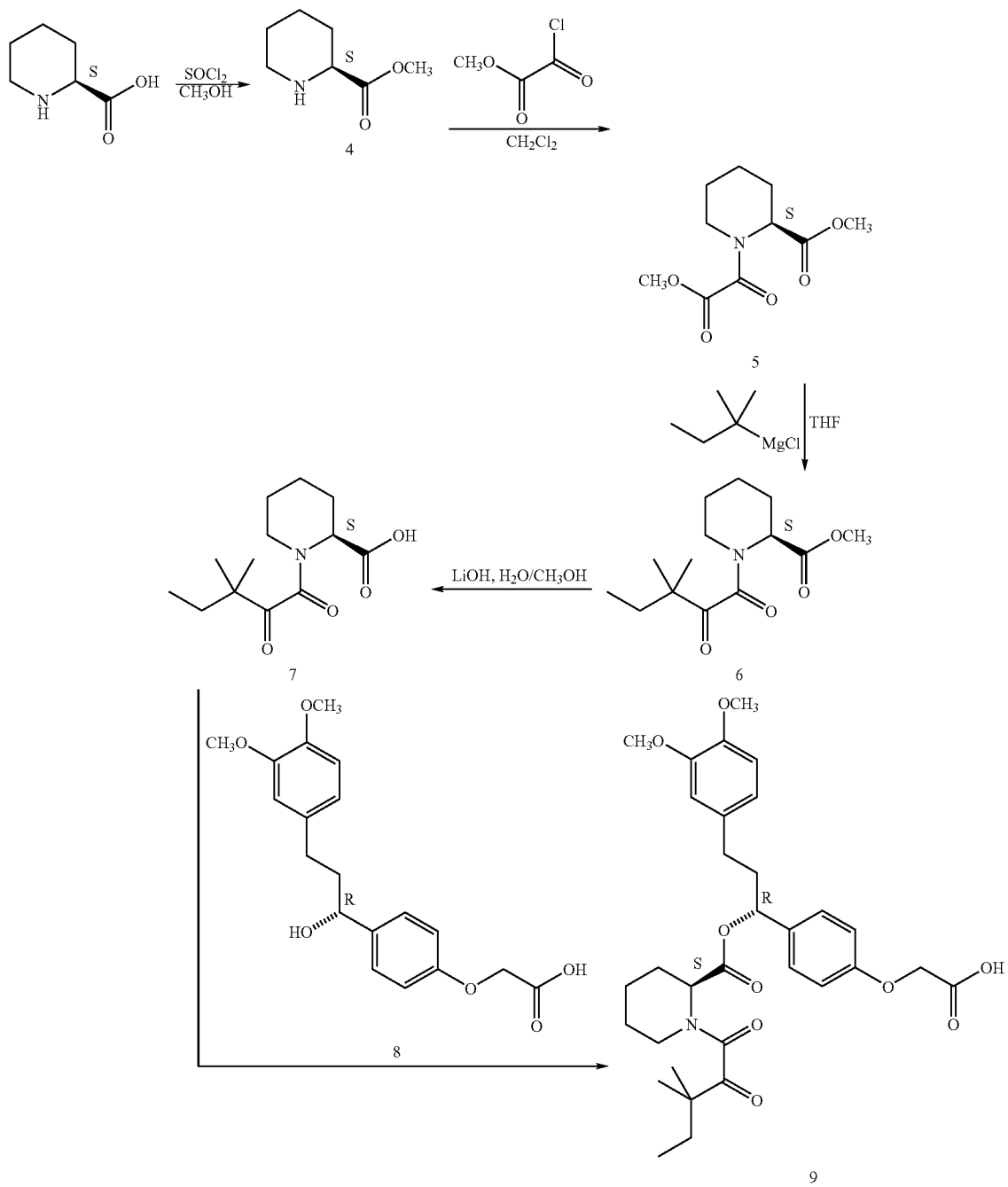

The procedures used were as follows.

Piperidine-2-carboxylic acid methyl ester (4). To a suspension of (S)-(−)-2-piperidinecarboxylic acid in methanol (30 mL) at −5° C. under a positive pressure of dry argon, thionyl chloride (1.25 mL, 17.1 mmol) was added in dropwise manner. Thereafter the suspension was slowly warmed to 40° C. and further stirred at 40° C. for 7 hours. The solvent was then evaporated to yield 2.7 g of white powder, whose structure was confirmed as that of piperidine-2-carboxylic acid methyl ester by $^1$H NMR (D$_2$O, 300 MHz): δ 1.61-1.94 (m, 5H), 2.29-2.35 (dd, J=2.6 Hz & 13.2 Hz, 1H), 3.02-3.12 (dt, J=2.5 Hz, 9.0 Hz, 1H), 3.45-3.52 (m, 1H), 3.85 (s, 3H, Me), 4.04-4.10 (dd, J=3.3 Hz, 11.4 Hz, 1H). $^{13}$C NMR (D$_2$O, 75 MHz): δ 21.21, 21.37, 25.61, 44.15, 53.63, 56.80, 170.21.

1-Methoxyoxalyl-piperidine-2-carboxylic acid methyl ester (5). Piperidine-2-carboxylic acid methyl ester (4) (1 g, 6.98 mmol) and dimethylaminopyridine (DMAP), 256 mg, 2.1 mmol, 0.3 eq) were dissolved in 10 mL of dry methylene chloride. The solution was cooled to 0° C. and 1.7 mL (20.95 mmol, 3 eq) dry pyridine was added, followed by dropwise addition of 2 mL (21.7 mmol, 3.1 eq) of methyl chlorooxoacetate. The solution was allowed to warm to room temperature and stirred for 22 h. The reaction was worked up by addition of saturated aqueous NaHCO$_3$ solution and was extracted three times with CH$_2$Cl$_2$, dried over Na$_2$SO$_4$, filtered and concentrated. The remaining pyridine was removed under vacuum. Chromatography of the crude product (20-40% ethyl acetate/hexanes) yielded 1.0936 mg (68%) of a colorless oil. The structure of the product was verified as that of 1-methoxyoxalyl-piperidine-2-carboxylic acid methyl ester by $^1$H NMR (CDCl$_3$, 300 MHz): δ 1.32-1.78 (m, 5H), 2.24-2.30 (m, 1H), 3.26-3.36 (dt, J=3.2 Hz, 13.1 Hz, 1H), 3.53-3.58 (m, 1H), 3.74 (s, 3H, Me), 3.86 (s, 3H, Me), 5.21-5.23 (brd, J=5.4 Hz, 1H). $^{13}$C NMR (CDCl$_3$, 75 MHz): δ 20.93, 25.01, 26.35, 44.31, 51.62, 52.47, 56.65, 161.34, 162.99, 170.48.

(2S)-1-(3,3-dimethyl-1,2-dioxopentyl)-2-piperidinecarboxylic acid methyl ester (6). 1-Methoxyoxalyl-piperidine-2-carboxylic acid methylester (5) (746.2 mg, 3.26 mmol) was dissolved in anhydrous tetrahydrofuran (15 mL), cooled to −78° C., and treated with 1,1-dimethylpropylmagnesium chloride (1.0 M, 6.5 mL). The reaction mixture was allowed to stir for 3 h at the same temperature under argon atmosphere, then quenched with saturated aqueous solution of NH$_4$Cl. 10 mL of ethyl acetate added to the quenched reaction mixture, the organic phase washed with water (3×15 mL), dried over Na$_2$SO$_4$, and the solvent evaporated and purified by flash chromatography (16-32% ethyl acetate:hexanes) to provide a clear oil, 578 mg, for a yield of 66%. The structure of the product was verified as that of (2S)-1-(3,3-dimethyl-1,2-dioxopentyl)-2-piperidinecarboxylic acid methyl ester by $^1$H NMR (CDCl$_3$, 300 MHz): δ 0.83-0.88 (t, J=7.5 Hz, 3H, Me), 1.17 (s, 3H, Me), 1.21 (s, 3H, Me), 1.56-1.76 (m, 5H), 2.25-2.30 (m, 1H), 3.13-3.23 (dt, J=3.2 Hz, 12.9 Hz, 1H), 3.34-3.38 (m, 1H), 3.73 (s, 3H, Me), 5.21-5.23 (brd, J=5.3 Hz, 1H). $^{13}$C NMR (CDCl$_3$, 75 MHz): δ 8.69, 21.14, 22.92, 23.59, 24.88, 26.32, 32.47, 43.93, 46.74, 51.12, 52.34, 167.53, 170.84, 207.78.

(2S)-1-(3,3-Dimethyl-1,2-dioxopentyl)-2-piperidinecarboxylic acid (7). (2S)-1-(3,3-dimethyl-1,2-dioxopentyl)-2-piperidinecarboxylic acid methyl ester (6) (570 mg, 2.1 mmol) in MeOH (15 mL) was treated with aqueous LiOH (76.2 mg in 7 mL of water) at 0° C. and the reaction mixture was stirred at room temperature for 2 h. Most of the methanol was then evaporated under reduced pressure and the resulting solution was partitioned between 1M HCl and ethyl acetate. The aqueous layer was extracted twice with methylene chloride and the combined organic extracts were dried over anhydrous sodium sulfate and concentrated to yield a white powder. The structure of the product was verified as that of (2S)-1-(3,3-dimethyl-1,2-dioxopentyl)-2-piperidinecarboxylic acid by $^1$H NMR (CDCl$_3$, 300 MHz): δ 0.84-0.88 (t, J=7.4 Hz, 3H, Me), 1.20 (s, 3H, Me), 1.23 (s, 3H, Me), 1.67-1.84 (m, 5H), 2.32-2.37 (brd, J=13.94 Hz, 1H), 3.2.0-3.28 (m, 1H), 3.40-3.44 (brd, J=12.92 Hz, 1H), 5.32-5.34 (brd, J=5.29 Hz, 1H). $^{13}$C NMR (CDCl$_3$, 75 MHz): δ 8.91, 21.34, 23.19, 23.76, 25.02, 26.41, 32.67, 44.22, 47.00, 51.20, 167.87, 175.97, 207.87.

(1R)-1-[4-(Carboxymethoxy)phenyl]-3-(3,4-dimethoxyphenyl)-1-propanol (8). Following the procedure described by Keenan, T., et al., "Synthesis and Activity of Bivalent FKBP12 Ligands for the Regulated Dimerization of Proteins," Bioorganic & Medicinal Chemistry, 1998, 6, 1309-1335, 3,4-dimethoxyphenyl aldehyde was reacted with 3'-hydroxy-acetophenone in the presence of KOH, and water/ethanol at 0° C., followed by reaction with H$_2$ in the presence of a Lindlar catalyst and methanol, to form the alcohol. The alcohol was then reacted with tert-butyl bromoacetate and K$_2$CO$_3$ in dimethyl formamide at 0° C., and then with trifluoroacetic acid in methylene chloride at 0° C.

(1R)-1-[4-(Carboxymethoxy)phenyl]-3-(3,4-dimethoxyphenyl)-1-propanyl (2S)-1-(3,3-dimethyl-1,2-dioxopentyl)-2-piperidinecarboxylate (9). Following the procedure described by Keenan et al. above, (1R)-1-[4-(carboxymethoxy)phenyl]-3-(3,4-dimethoxy-phenyl)-1-propanol was reacted with pipecolyl acid in the presence of dicyclohexyl carbodiimide (DCC), dimethylaminopyridine (DMAP), and methylene chloride at 0° C. to yield the title compound (9).

Example 4

Screening of Candidates for the Chaperone Binding Portion

The following four compounds, synthesized as described in, or in a manner analogous to the description in, Example 3, were tested for their suitability as candidates for the chaperone binding portion of the construct of this invention. The chaperone to which binding was evaluated was FKBP12 and, screening was performed by ELISA.

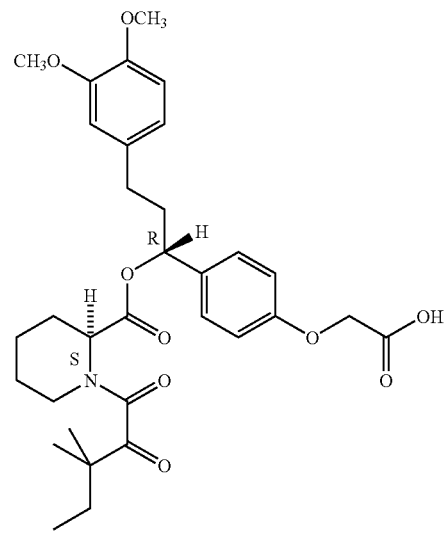

9-RS

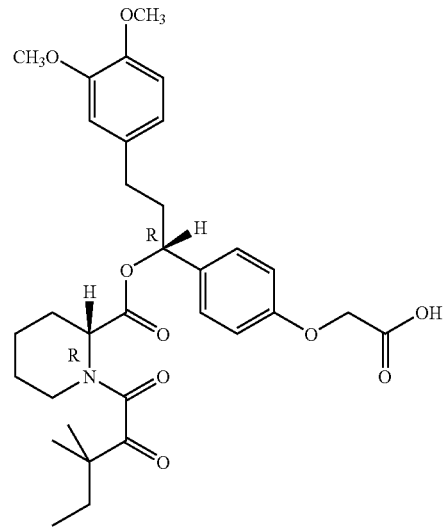

9-RR

-continued

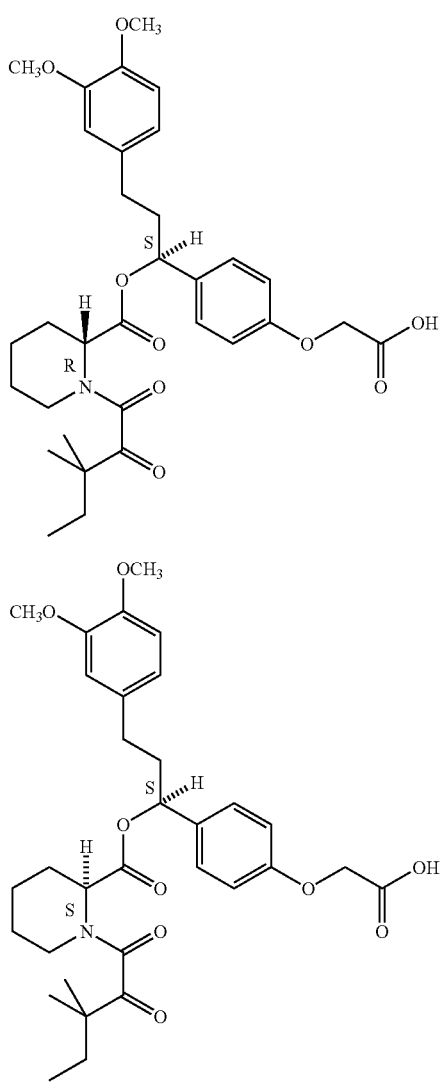

9-SR

9-SS

Step 1. Sample Solutions. Four samples of each of the test compounds were prepared by dissolving the compounds in the coating buffer described in Example 2 to a final concentration of 1 μM.

Step 2. Coating the Plate. The wells of a 96-well microtiter plate were coated with the sample solutions at 100 μL/well. The plates were then sealed and allowed to incubate at 4° C. for at least 8 hours.

Step 3. Washing the Plate. The coating solution was removed from the wells and the plate was washed two times with the washing solution of Example 2 at 300 μL/well.

Step 4. Blocking. The blocking buffer used in Example 2 was added at a volume of 150 μL/well, and the plate was incubated at room temperature for 2 hours.

Step 5. Sampling. Biotin-labeled FKBP12 was dissolved in a binding buffer to form a 1 μM solution. The binding buffer was a mixture of a coating buffer with the blocking buffer of Step 4 in a 90:10 ratio by volume. The coating buffer consisted of 50 mM Tris (Trizma Base from Sigma-Aldrich), 150 mM NaCl, 1 mM $CaCl_2$, 1mM $MgCl_2$, 1 mM $MnCl_2$, pH=7.4 in redistilled water. Once blocking had been completed in Step 4, the blocking buffer was removed from each well, and the biotin-labeled amyloid β solution was placed in one of the wells for each of the four test compounds, together with additional blocking buffer for a total volume of 125 μL in the well. Dilutions were then prepared to achieve final concentrations per well of 40 μM, 30 μM, 20 μM, 10 μM, 5 μM, and 1 μM. The dilutions were performed in quadruplicate, thus resulting in four sets of wells for each test compound. The procedures used for cloning, expression, and purification of FKBP12 are provided at the end of this example.

Step 6. Mixing. The solution in each well was mixed by being drawn into and ejected from a pipette 15 times. The plate was then gently agitated to achieve thorough mixing. After mixing, the plate was covered and incubated at room temperature overnight.

Step 7. Washing. The solution in each well was discarded and the plate was washed three times with 170 μL/well of the washing solution of Example 2.

Step 8. Binding with avidin-HRP. NeutrAvidinHRP solution was added to each well at 0.01 μg (100 μL)/well. The wells were then covered and incubated at room temperature for 30 minutes.

Step 9. Substrate addition. The solution in each well was discarded and the plate was washed 3 times with the above-referenced washing solution at 170 μL/well of washing solution. A chemiluminescent substrate solution was then added at 100 μL/well.

Step 10. Fluorescence measurement and calculations. Luminescence was read as in Example 2, and the results are shown in Table III below.

TABLE III

ELISA Test Results for Candidates for Chaperone Binding Portion

| Concentration (μM/well) | Test Compound: | Average Luminescence Concentration (CPS) | | | |
|---|---|---|---|---|---|
| | | 9-RR | 9-RS | 9-SR | 9-SS |
| 40 | | 1138 | 5509 | 1392 | 1231 |
| 30 | | 1297 | 4244 | 1478 | 1366 |
| 20 | | 371 | 2006 | 1410 | 579 |
| 10 | | 769 | 1685 | 1218 | 931 |
| 5 | | 1158 | 1688 | 1050 | 876 |
| 1 | | 660 | 1399 | 762 | 297 |

Since the optimal chaperone binding portion for the construct of this invention is one with low or moderate binding affinity, the optimal candidates among the four tested in this example are 9-RR and 9-SS.

Procedures for Cloning, Expression and Purification of Molecular Chaperon Human FKBP12.

Construction of FKBP 12 Gene

1. PCR amplification of the EST Clone (IMAGE) contained the FKBP 12

```
Primer-F:   5'-CACCATGGGAGTGCAGGTGGAAACCA-3'
Primer-R:   5'-TCATTCCAGTTTTAGAAGCTCCACATC-3'
```

Human FKBP cDNA (IMAGE Human Clone ID: 683981) as a template

Using Taq polymerase that is Platinum Taq DNA Polymerase High Fidelity from Invitrogen (Catalog #: 11304-011)

2. Cloning FKBP12 gene using pENTR/SD Directional TOPO Cloning Kit (Invitrogen Inc. Catalog #: K2420-20)
Using Invitrogen Gateway system to clone human FKBP12 gene
3. Check the FKBP12 DNA sequence after PCR reaction
Human FKBP12 DNA sequence:

```
atgggagtgc aggtggaaac catctcccca ggagacgggc gcaccttccc caagcgcggc cagacctgcg tggtgcacta caccgggatg cttgaagatg gaaagaaatt tgattcctcc cgggacagaa acaagccctt taagtttatg ctaggcaagc aggaggtgat ccgaggctgg gaagaagggg ttgcccagat gagtgtgggt cagagagcca aactgactat atctccagat tatgcctatg gtgccactgg gcacccaggc atcatcccac cacatgccac tctcgtcttc gatgtggagc ttctaaaact ggaatga
```

Expression and Purification of Human FKPB12 Protein.
1. Human FKBP 12 was transformed into BL21-AI
2. Pilot Expression:
Pick 3-4 transformants from BL21-AI
Culture them in 5 mL of LB+Carbenicill, at 37° C. until OD600-0.6 to 1.0 (4 Hours)
Use the culture to inoculate fresh LB+Carenicillin (1:20 dilution of the initial culture Grow until Mid-log phase (OD600 0.4 2-3 hours)
Split each culture into two cultures, add arabinose to one of the culture (induced); the other one is uninduced.
Remove a 500 µL aliquot from each culture as a zero time point samples
Continue to incubate the cultures, take time points for each culture every hour for 4 hours
3. The recombinant His-FKBP12 protein was purified using Ni-NTA column and L-arabinose in *E. Coli* Expression system with Gateway Technology.
4. Preparing Samples for soluble/insoluble proteins, running polyacrylamide Gel Electrophoresis, then analyzing samples
Protein PAGE gel—stain with Coomassie G-250
Western blot anti FKBP12 antibody & 6xHis antibody to identify the human FKBP 12 protein.

Example 5

Synthesis of a Labeled Bifunctional Molecule of the Invention with β-Amyloid and Chaperone Binding Portions The products of Examples 1 and 3 were joined by a lysine linker and a fluorescent marker joined to the linker by a three-stage reaction scheme. In the first stage, β-amyloid binding compound of Example 1 was bonded to a lysine linker; in the second stage, a chaperone binding compound of Example 3 was bonded to the linker-derivatized β-amyloid binding portion; and in the third stage, the marker was bonded to the linker. The syntheses were performed as follows:

First Stage: Attachment of Lysine Linker to β-Amyloid Binding Portion.

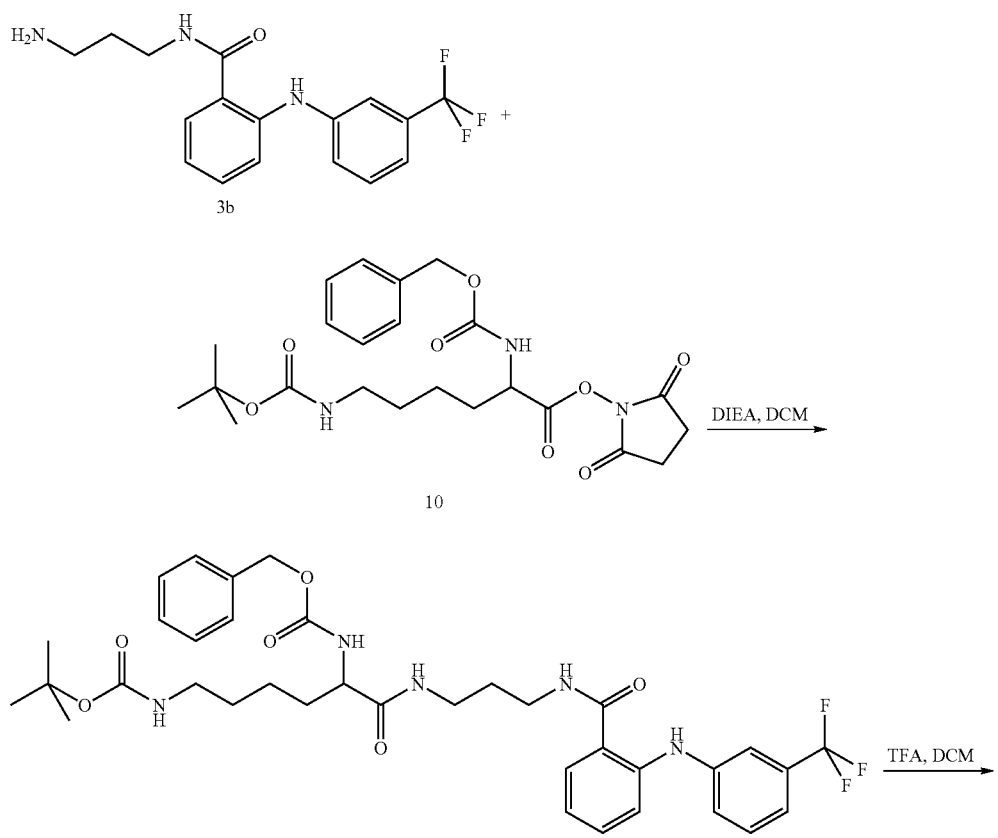

-continued

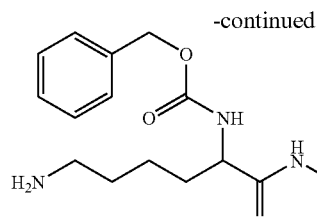
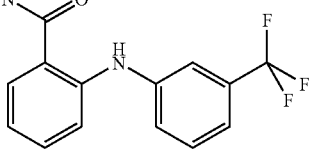

12

15

The first reaction shown above was performed by adding N,N-diisopropyl-ethylamine (DIEA) (1.23 mL, 7.08 mmol) to a solution of N-(2-amino-propyl)-2-(3-trifluoromethyl-phenylamino)-benzamide (3b) (597 mg, 1.77 mmol) and Z-Lys(Boc)-OSu (10) (846 mg, 1.77 mmol) in dichloromethane, and stirring the resulting reaction mixture at room temperature for 24 h. The product was washed with water, dried over $Na_2SO_4$, and the solvent evaporated and flashed over silica gel (ethanol:$CH_2Cl_2$, 0-28%) to give a white powder, m.p. 140.6-141° C. The product was identified as 6-tert-butoxycarbonylamino-2-{3-[2-(3-trifluoromethyl-phenylamino)-benzoylamino]-propylcarbamoyl}-hexanoic acid benzyl ester (11) by $^1$H NMR ($CDCl_3$, 300 MHz): δ 1.22-1.81 (m, 17H), 3.02-304 (m, 2H, $CH_2$), 3.28-3.41 (m, 4H, $2CH_2$), 4.13 (m, 1H, CH), 4.77 (brs, 1H, N—H), 5.03 (s, 2H, $CH_2$), 5.87 (brs, 1H, N—H), 6.79-6.84 (t, J=7.9 Hz, 1H), 7.04-7.51 (m, 11H), 7.56-7.58 (d, J=7.6 Hz, 1H). $^{13}$C NMR ($CDCl_3$, 75 MHz): δ 22.68, 28.48, 29.55, 29.70, 32.00, 36.01, 36.24, 39.82, 55.40, 67.16, 79.36, 115.91, 116.16 (q, J=3.7 Hz), 118.23 (q, J=3.7 Hz), 119.38, 122.83, 124.18 (q, 272 Hz), 128.12, 128.17, 128.30, 128.59, 129.88, 131.72 (q, 32 Hz), 132.26, 136.25, 142.67, 144.37, 156.50, 169.68, 173.21.

The second reaction was performed by adding trifluoroacetic acid to a solution of 6-tert-butoxycarbonylamino-2-{3-[2-(3-trifluoromethyl-phenylamino)-benzoylamino]-propyl-carbamoyl}-hexanoic acid benzyl ester (11) in dichloromethane, and stirring for 2 h at room temperature. The solvent was then evaporated to yield a colorless liquid, quantitatively. The liquid was identified as (5-amino-1-{3-[2-(3-trifluoromethyl-phenylamino)-benzoylamino]-propylcarbamoyl}-carbamic acid benzyl ester (12) by $^1$H NMR ($CDCl_3$, 300 MHz): δ 1.42-1.52 (m, 8H), 3.19-3.36 (m, 4H), 4.04-4.09 (dd, J=5.02 & 8.91 Hz, 1H), 2.87-2.92 (t, J=7.4 Hz, 3H), 5.07 (s, 2H), 6.93-6.99 (m, 1H), 7.16-7.43 (m, 13H), 7.62-7.64 (d, J=7.5 Hz, 1H). $^{13}$C NMR ($CD_3OD$, 75 MHz): δ 22.48, 26.66, 28.75, 31.12, 36.05, 36.20, 39.06, 39.16, 55.14, 66.46, 112.76, 114.42 (q, J=3.7 Hz), 116.52, 116.97, 177.12 (q, J=3.7 Hz), 120.05, 121.49, 121.78, 124.21 (q, J=272 Hz), 127.54, 127.67, 128.05, 128.50, 129.61, 129.80, 130.64, 131.28 (q, J=32 Hz), 131.69, 136.64, 142.76, 143.44, 170.11, 173.51.

Second stage: Attachment of chaperone binding portion of Example 2.

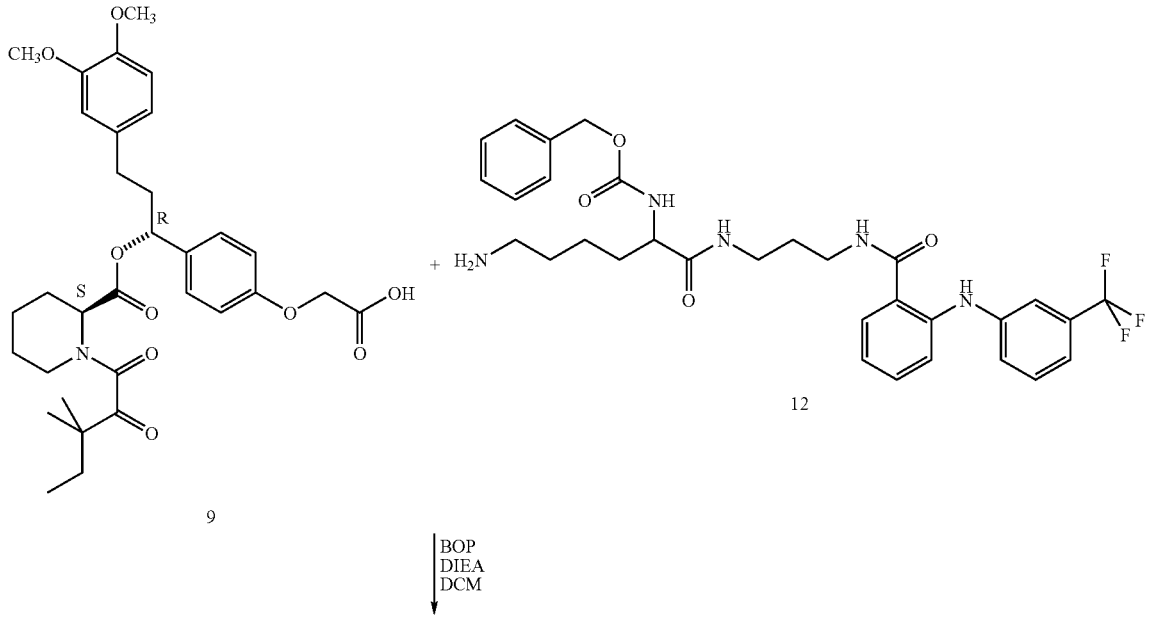

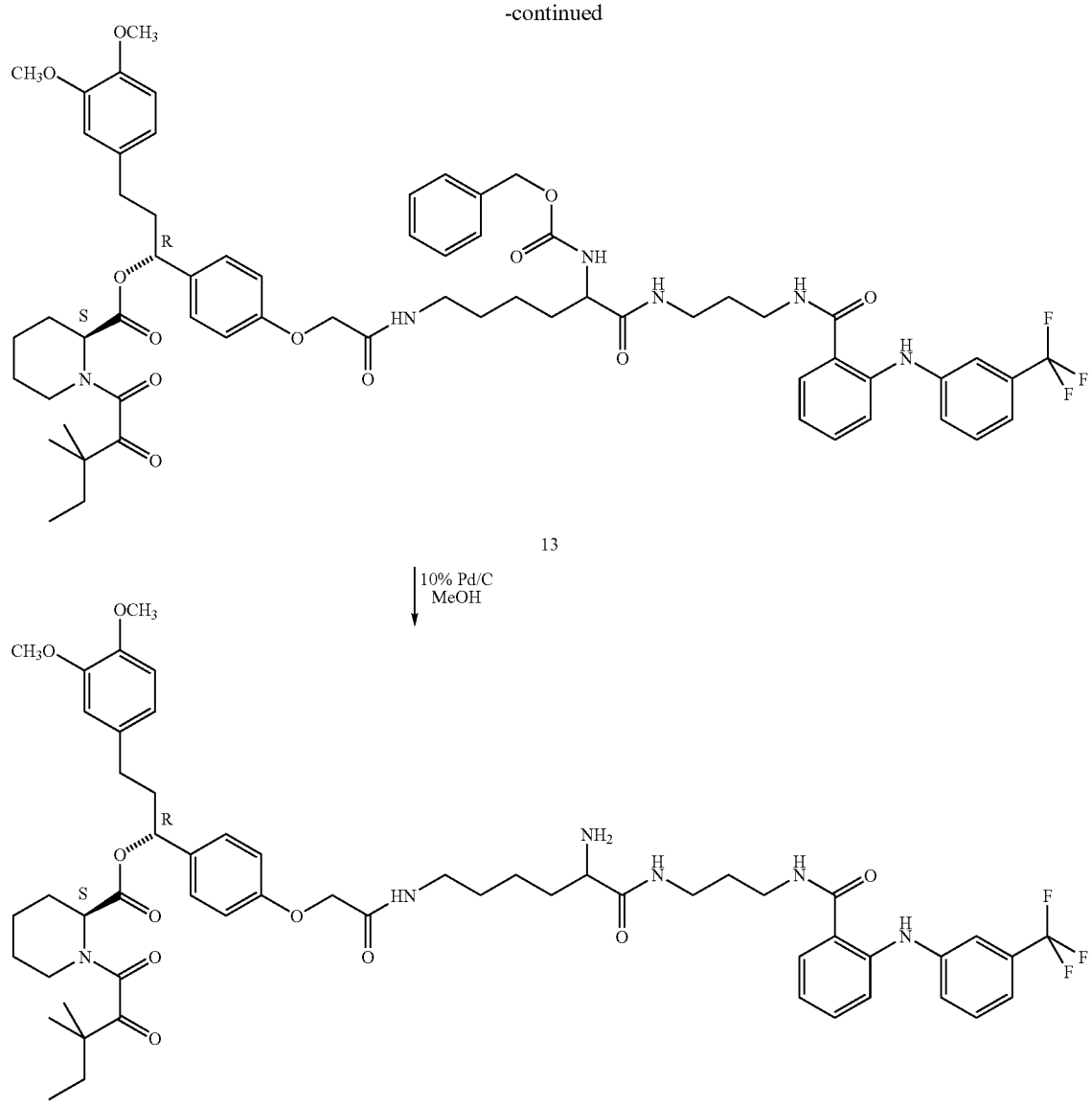

13

↓ 10% Pd/C
MeOH

14

The first reaction shown above was performed by adding BOP reagent (benzotriazol-1-yl-oxy-tris-(dimethylamino) phosphonium hexafluorophosphate, 204.6 mg, 0.45 mmol) and diisopropylethyl amine (161.1 μL, 0.93 mmol) to a stirred solution of (1R)-1-[4-(carboxymethoxy)phenyl]-3-(3,4-dimethoxy-phenyl)-1-propanyl (2S)-1-(3,3-dimethyl-1,2-dioxopentyl)-2-piperidinecarboxylate (9, 0.15 mmol, 90 mg) and stirring for 30 min at 0° C., followed by the addition of (5-amino-1-{3-[2-(3-trifluoromethyl-phenylamino)-benzoylamino]-propylcarbamoyl}-carbamic acid benzyl ester (12, 99.0 mg, 0.17 mmol). The resulting reaction mixture was warmed to room temperature and stirred overnight. The mixture was then washed with saturated aqueous NaHCO$_3$ (10 mL×2) and water (10 mL×2), and the solvent was evaporated and the residue purified by flash chromatography over silica gel (methanol:CH$_2$Cl$_2$, 0-6%) to give 141.7 mg of a colorless oil, (81% yield). The oil was identified as 1-(3,3-dimethyl-2-oxo-pentanoyl)-piperidine-2-carboxylic acid-1-{4-[(5-benzyloxycarbonylamino-5-{3-[2-(3-trifluoromethyl-phenylamino)-benzoylamino]-propylcarbamoyl}-pentylcarbamoyl)-methoxy]-phenyl}-3-(3,4-dimethoxy-phenyl)-propyl ester (13) by $^1$H NMR (CDCl$_3$, 300 MHz): δ 0.88 (t, J=7.5 Hz, 3H), 1.12 (s, 3H), 1.13 (s, 3H), 1.38-1.76 (m, 17H), 1.86-1.92 (m, 1H), 2.27-2.37 (m, 2H), 2.49-2.59 (m, 2H), 3.09-3.18 (m, 1H), 3.26-3.41 (m, 6H), 3.85 (s, 3H), 3.86 (s, 3H), 4.42 (s, 2H), 5.09 (s, 2H), 5.27 (brd, J=4.5 Hz, 1H), 5.60 (brs, 1H), 5.76 (t, J=6.8 Hz, 1H), 6.66-6.89 (m, 6H), 7.17-7.43 (m, 13H), 7.60 (d, J=7.8 Hz, 1H). $^{13}$C NMR (CDCl$_3$, 75 MHz): δ 21.12, 22.36, 23.08, 23.39, 24.86, 26.36, 28.91, 29.39, 31.27, 31.56, 32.38, 35.75, 35.99, 37.85, 38.03, 44.07, 46.61, 51.24, 55.79, 55.87, 67.01, 67.34, 76.31, 111.36, 111.76, 114.71, 115.70, 116.02, 118.13, 119.11, 119.18, 120.12, 122.73, 124.02, 127.95, 128.15, 128.27, 128.45, 129.78, 131.51, 132.15, 133.34, 133.46, 136.11, 142.47, 144.26, 147.37, 148.88, 156.92, 167.24, 168.38, 169.50, 169.59, 172.80, 207.75.

The second reaction was performed by hydrogenating a solution of 13 (65 mg, 0.06 mmol) and 10% Pd/C (10% w/w) in methanol at 15 psi pressure of H$_2$ in a Parr hydrogenator for 4 h. The reaction mixture was then filtered through a pad of Celite to remove the catalyst. The filtrate was concentrated and chromatographed (Sigel, methanol:CH$_2$Cl$_2$, 6-8%) to give 11.3 mg of a colorless oil (18% yield). The oil was identified as 1-(3,3-dimethyl-2-oxo-pentanoyl)-piperidine- 2-carboxylic acid-1-{4-[(5-amino-5-{3-[2-(3-trifluoromethyl-phenylamino)-benzoylamino]-propylcarbamoyl}-pentylcarbamoyl)-methoxy]-phenyl}-3-(3,4-dimethoxy-phenyl)-propyl ester (14) by ¹H NMR (CDCl₃, 300 MHz): δ 0.80 & 0.88 (t, J=7.5 Hz, 3H, for two rotamers), 1.12-1.13 and 1.16-1.20, (two singlets, 6H, Me, for the two rotamers), 1.22-2.66 (m, 31H), 3.09-3.17 (m, 1H), 3.37-3.49 (m, 8H), 3.84 (s, 6H), 4.47 (s, 2H), 5.28 (d, J=5.0 Hz, 1H), 5.76 (t, J=7.0 Hz, 1H), 6.66-6.91 (m, 8H), 7.17-7.20 (m, 1H, 7.29-7.43 (m, 7H), 7.61-7.67 (m, 3H). ¹³C NMR (CDCl₃, 75 MHz): δ 21.19, 22.93, 23.15, 23.48, 24.94, 26.43, 29.39, 29.65, 31.33, 32.47, 34.46, 35.75, 37.93, 38.57, 44.69, 46.69, 51.28, 54.94, 55.86, 55.94, 67.42, 76.35, 111.38, 111.79, 114.77, 115.73, 116.12, 118.11, 119.21, 119.28, 120.16, 122.28, 122.67, 125.88, 128.03, 128.36, 129.73, 131.43, 131.86, 132.10, 133.39, 133.55, 142.61, 144.36, 147.43, 148.95, 157.06, 167.27, 168.15, 169.36, 169.68, 207.79.
Third Stage: Attachment of Fluorescent Label.
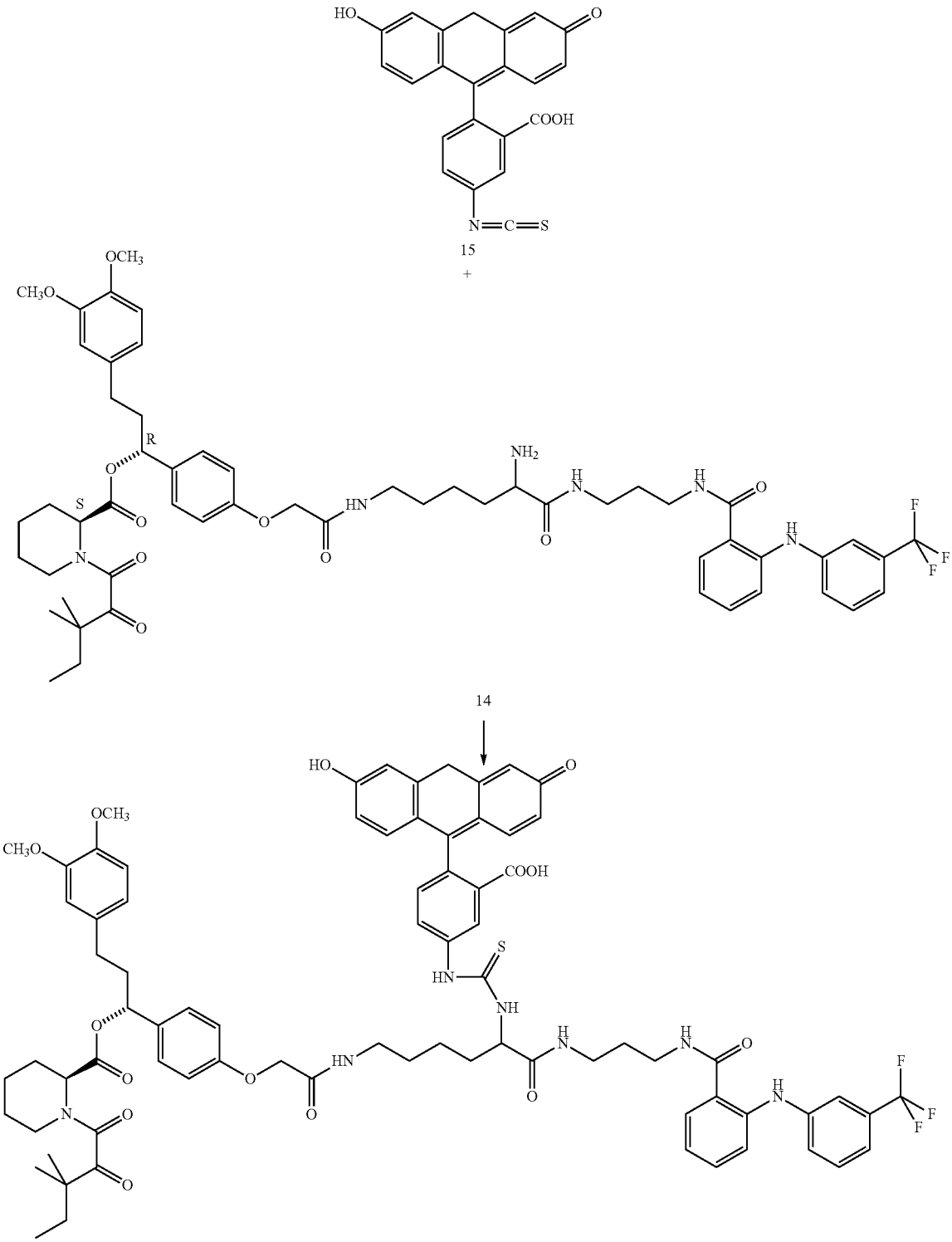

This reaction was performed by dissolving 1-(3,3-dimethyl-2-oxo-pentanoyl)-piperidine-2-carboxylic acid-1-{4-[(5-amino-5-{3-[2-(3-trifluoromethyl-phenylamino)-benzoylamino]-propylcarbamoyl}-pentylcarbamoyl)-methoxy]-phenyl}-3-(3,4-dimethoxy-phenyl)-propyl ester (14) in dimethyl formamide, adding triethylamine and fluorescein isothiocyanate (15), and stirring for 70 h at room temperature. The resulting mixture was concentrated to afford crude product which was purified by flash chromatography, silica gel (methanol:$CH_2Cl_2$; 0-10%), to yield a yellow powder, 17 mg, 52% yield. The identity of the product was confirmed as that shown (16) by $^1$H NMR ($CDCl_3$, 300 MHz): δ 0.85 (t, J=7.4H, 3H), 1.17 (s, 3H), 1.18 (s, 3H), 1.35-1.99 (m, 15H), 2.19-2.30 (m, 2H), 2.47-2.54 (m, 2H), 3.02-3.19 (m, 1H), 3.76 (s, 3H), 3.77 (s, 3H), 4.47 (s, 2H), 4.63 (brs, 1H), 5.15 (brd, J=4.1 Hz, 1H), 5.64-5.69 (m, 1H), 6.49-6.52 (dd, J=2.0 & 8.7 Hz, 1H), 6.65-7.39 (m, 21H), 7.61 (d, J=7.6 Hz. 1H), 7.80 (d, J=8.4 Hz, 1H), 8.25 (brs, 1H). $^{13}$C NMR ($CDCl_3$, 75 MHz): δ 22.23, 23.75, 24.04, 24.18, 26.03, 27.50, 30.22, 30.34, 32.48, 33.14, 33.69, 37.63, 37.92, 39.02, 39.79, 45.80, 47.82, 52.96, 56.62, 56.72, 59.58, 68.47, 78.04, 103.76, 112.54, 113.43, 113.76, 115.23, 115.90, 116.09, 118.41, 118.67, 120.76, 127.57, 121.86, 123.06, 123.31, 123.94, 126.56, 127.54, 129.58, 130.08, 130.70, 130.89, 131.35, 132.98, 133.19, 134.79, 135.41, 142.58, 144.27, 144.91, 148.95, 150.54, 155.19, 159.18, 169.21, 171.10, 171.62, 174.79, 183.36, 209.15.

While the foregoing description describes various alternatives, still further alternatives will be apparent to those who are skilled in the art and are within the scope of the invention.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A bifunctional molecule for imaging a target protein in vivo, said biofunctional molecule consisting of a first moiety having binding specificity and affinity for said target protein, a second moiety having binding specificity and affinity for a chaperone protein, a linking group joining said first and second moieties, and a detectable label, said affinity of said first moiety for said target protein being substantially stronger than said affinity of said second moiety for said chaperone such that detection of said label indicates the presence of said target protein, wherein said first moiety is chosen from

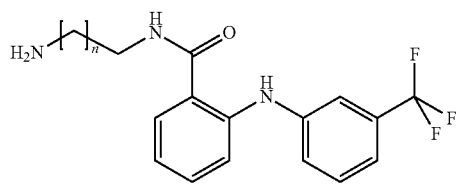

where n is 1, 2, 3, or 4; and said second moiety is chosen from

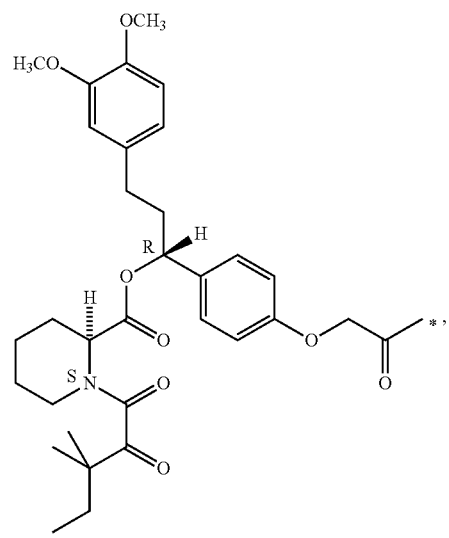

9-RS

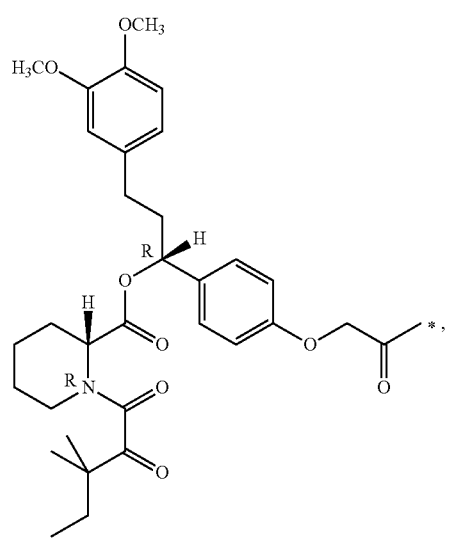

9-RR

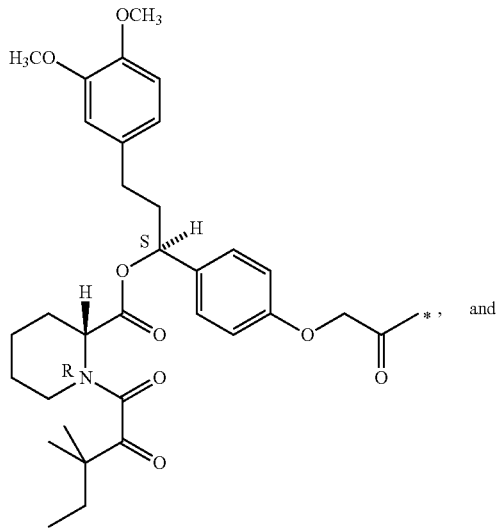

9-SR and

9-SS

[Structure: 9-SS isomer diagram]

2. The bifunctional molecule of claim 1 wherein said second moiety is a member select from the group consisting of residues of 9-RR, 9-SR, and 9-SS isomers of (1R)-1-[4-(carboxymethoxy)phenyl]-3-(3,4-dimethoxy-phenyl)-1-propanyl (2S)-1-(3,3-dimethyl-1,2-dioxopentyl)-2-piperidincarboxylate.

3. The bifunction molecule of claim 1 wherein the detectable label is a member selected from the group consisting of fluorophores, radioactive isotopes, and magnetic resonance imaging contrast agents.

4. The bifunctional molecule of claim 1 wherein the detectable label is a fluorophore.

5. The bifunctional molecule of claim 1 wherein said linking group is a member selected from the group consisting of saturated and unsaturated hydrocarbon chains, saturated hydrocarbon chains interrupted or terminated with O atoms, hydrocarbon chains interrupted or terminated with N atoms, residues of amino acids, peptides, and carbohydrates.

6. The bifunctional molecule of claim 1 wherein said linking group is a member selected from the group consisting of saturated and unsaturated hydrocarbon chains, saturated hydrocarbon chains interrupted or terminated with O atoms, hydrocarbon chains interrupted or terminated with N atoms, residues of amino acids.

7. The bifunctional molecule of claim 1 wherein said linking group is a saturated hydrocarbon chain of 3 to 5 carbon atoms terminated with amino groups.

8. The bifunctional molecule of claim 1 wherein said linking group is a lysine.

9. A bifunctional molecule of claim 1 wherein said bifunctiaonl bifunctional molecule has the formula

[Structure with $R^3$NH, $R^2$NH, $R^1$ substituents]

wherein $R^1$ is said first moiety chosen from

[Structure: $H_2N$-(CH$_2$)$_n$-NH-C(O)-phenyl-NH-phenyl-CF$_3$]

where n is 1, 2, 3, or 4, $R^2$ is said second moiety chosen from

9-RS

[Structure: 9-RS isomer diagram]

9-RR

[Structure: 9-RR isomer diagram]

-continued

9-SR

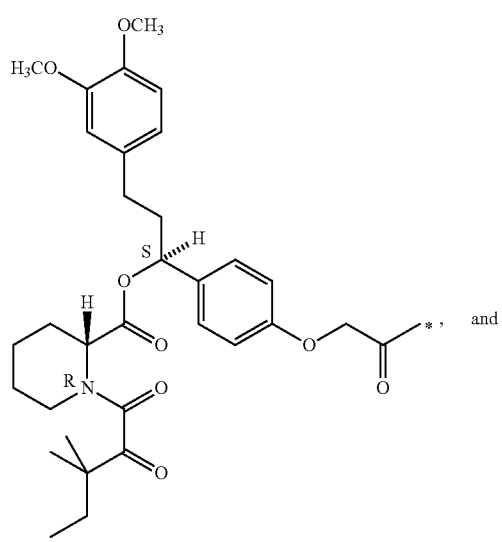

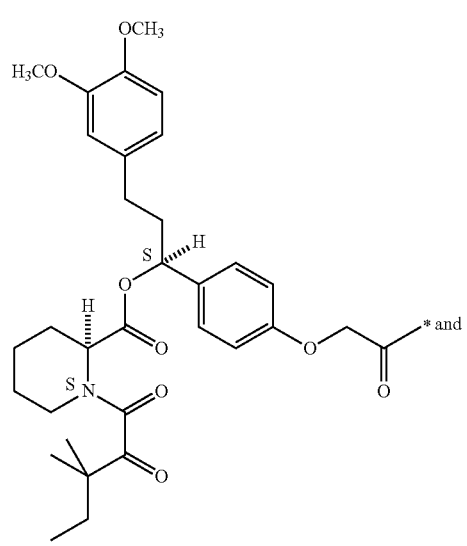

R³ is a detectable label.

10. The labeled bifunctional molecule of claim 9 wherein R³ is a fluorophore.

11. The bifunctional molecule of claim 9 wherein n is 2, 3, or 4.

12. The bifunctional molecule of claim 9 wherein n is 2 or 3.

13. The bifunctional molecule of claim 9 wherein n is 2.

14. The bifunctional molecule of claim 9 wherein R² is

9-RS

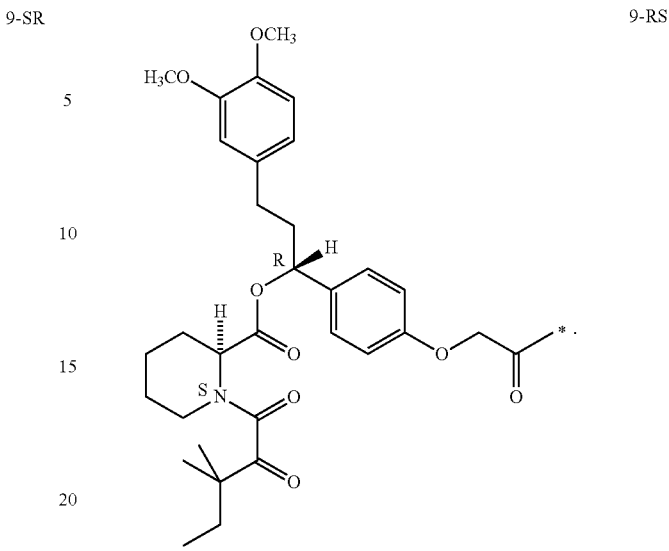

15. The bifunctional molecule of claim 9 wherein R² is chosen from

9-RR

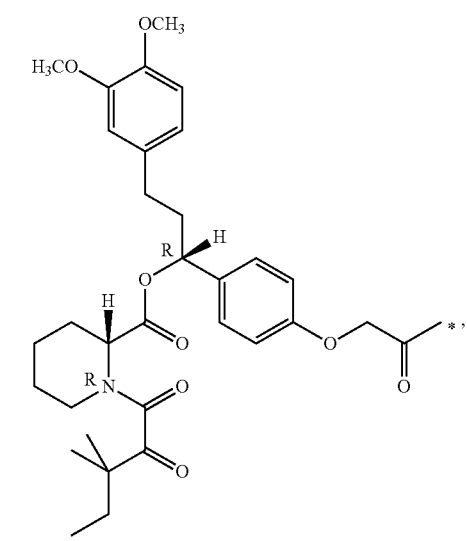

9-SR

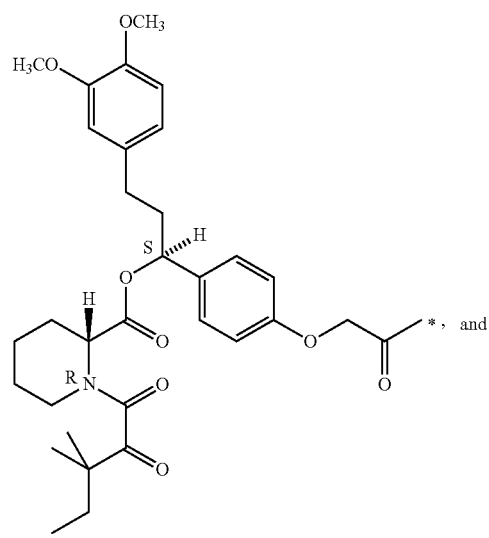

-continued
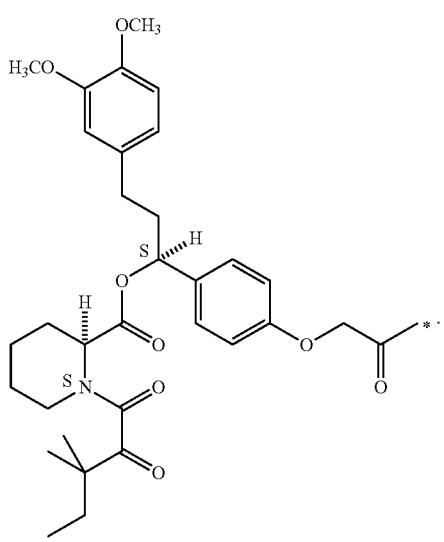
9-SS
16. The bifunctional molecule of claim 9 wherein $R_3$ is a fluorophore of the formula:
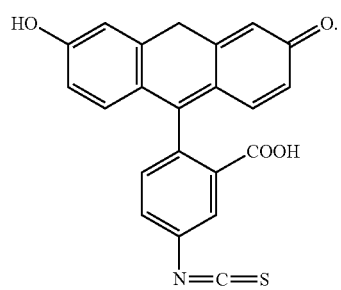
* * * * *